United States Patent [19]

Fost et al.

[11] Patent Number: 5,677,269

[45] Date of Patent: Oct. 14, 1997

[54] SILICONE CONTAINING IMIDAZOLINE COMPOSITIONS

[75] Inventors: Dennis L. Fost, Ridgewood; Abe Berger, Summit, both of N.J.

[73] Assignee: Mona Industries, Inc., Paterson, N.J.

[21] Appl. No.: 651,299

[22] Filed: May 22, 1996

Related U.S. Application Data

[60] Continuation-in-part of Ser. No. 611,068, Mar. 5, 1996, Pat. No. 5,633,221, which is a division of Ser. No. 304,563, Sep. 12, 1994, Pat. No. 5,496,478.

[51] Int. Cl.$^6$ .................. C01M 105/08; C07D 231/10
[52] U.S. Cl. ................ 508/210; 514/63; 548/10
[58] Field of Search ............... 548/110; 514/63; 508/210

[56] References Cited

U.S. PATENT DOCUMENTS 5,496,478 3/1996 Fost et al. ................ 548/110

*Primary Examiner*—Joseph McKane
*Attorney, Agent, or Firm*—Franklyn Schoenberg; Norman E. Lehrer

[57] ABSTRACT

Silicone containing imidazoline compositions are provided which are represented by the formula:

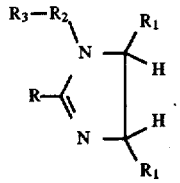

9 Claims, No Drawings

SILICONE CONTAINING IMIDAZOLINE COMPOSITIONS

RELATED APPLICATION

This application is a continuation-in-part of application Ser. No. 611,068, filed Mar. 5, 1996, now U.S. Pat. No. 5,633,221 which is a divisional application of application Ser. No. 304,563, filed Sep. 12, 1994, now U.S. Pat. No. 5,496,478.

FIELD OF THE INVENTION

The present invention relates to novel imidazoline compositions and, more particularly, to silicone containing imidazoline compositions and to methods for preparing the same.

BACKGROUND OF THE INVENTION

The production and marketing of imidazolines and various derivatives thereof has been carried on for a number of years. Such compositions have been widely used as surface active agents, metal and textile treating compounds and for a variety of other applications. Imidazolines are commonly prepared by condensing, under conditions of heating and stirring, a long chain aliphatic monocarboxylic or fatty acid or a source thereof such as amides (or esters of such acids) with an alkyl, hydroxyalkyl and/or aminoalkyl ethylene diamine derivative, such as hydroxyethyl ethylene diamine.

Organosiloxane compositions including a variety of derivatives thereof which exhibit excellent properties as surface active agents, lubricants and the like are also known and have been used commercially over the years. While a variety of imidazoline and polysiloxane compositions and derivatives thereof are known, to the best of our knowledge there has been no disclosure or suggestion of the novel silicone-containing imidazoline compositions and methods for preparing the same herein described.

It is accordingly an object of the present invention to provide highly useful, novel silicone containing imidazoline compositions and the acid salts thereof.

It is a further object of the present invention to provide a method for directly and readily preparing silicone containing imidazoline compositions and the acid salts thereof.

In accordance with the present invention there are provided novel silicone containing imidazoline compositions that may be represented by the formula:

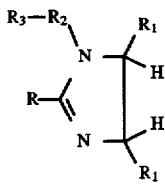

wherein:

R is an organosilicone backbone chain which may be represented by the formula:

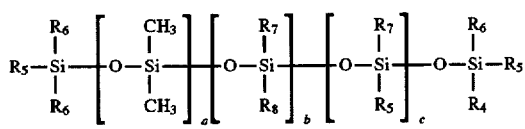

wherein:

$R_5$, which can be the same or different, can be selected from $R_6$, a pyrrolidone-containing group of the formula:

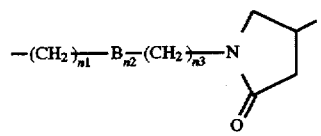

and mixtures thereof, wherein $R_6$ is as herein below defined, $n^1$ is zero or an integer from 1 to 12, $n^2$ is 0 or 1, $n^3$ is an integer from 1 to 5, and B is sulfur or oxygen with the proviso that when $n^2$ is 1, $n^1$ and $n^3$ each is at least 1; and with the further proviso that at least one of $R_5$ is a group of the formula:

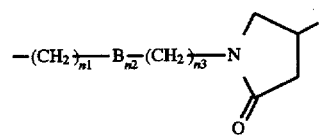

$R_6$ can be the same or different and can be selected from alkyl, aryl and olefin (vinyl);

$R_7$ and $R_8$, which can be the same or different, are selected from alkyl, aryl, capped or uncapped polyoxyalkylene, alkaryl, aralkylene and alkenyl (vinyl);

a can be an integer from 0 to 50,000;

b can be an integer from 0 to 5,000; and c can be an integer from 0 to 100;

$R_1$ which can be the same or different is of the group consisting of hydrogen and lower alkyl($C_{1-6}$);

$R_2$ is hydrogen or an alkylene hydrocarbon group; and $R_3$ can be selected from $-OH, -NH_2, R_9CONH-, R_9COO-$ and $-H$, wherein $R_9$ is saturated or unsaturated alkyl having from 1–22 carbon atoms.

The present invention is also concerned with acid salts of silicone-containing imidazoline compositions having anionic groups of valences from 1 to 3 which may be represented by the formula:

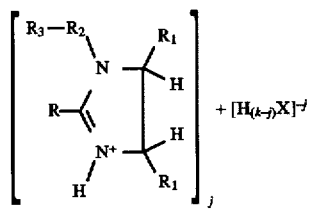

wherein:

R is as hereinabove defined;

$R_1$ and $R_2$ are as hereinabove described;

$R_3$ is as hereinabove defined;

X is an anion group having 1–3 valence;

j is an integer from 1 to 3; and k is an integer from 1–3; with the proviso that (k-j) is 0 or a positive integer.

In another aspect of the present invention, there is also provided a method for readily preparing silicone-containing imidazoline compositions having effective surface active, substantivity to a variety of materials, corrosion inhibition and lubrication properties which comprises reacting an organosilicone fluid or composition having at least one terminal, lateral or combination of terminal and lateral pyrrolidone-containing carboxyl functional groups with at least a stoichiometric amount of an alkyl, hydroxyalkyl and/or aminoalkyl ethylene diamine derivative at an elevated temperature, preferably at least about 140° C., for a time necessary to react the carboxyl functional group and provide for the cyclization of the reaction product.

DESCRIPTION OF THE PREFERRED EMBODIMENT

The present invention is concerned with novel and highly useful silicone-containing imidazoline compositions that can be represented by the formula:

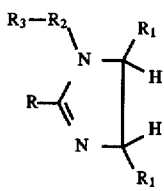

wherein:

R is an organosilicone backbone chain which may be represented by the formula:

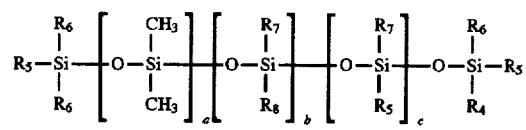

wherein:

$R_5$, which can be the same or different, can be selected from $R_6$, a pyrrolidone containing group of the formula:

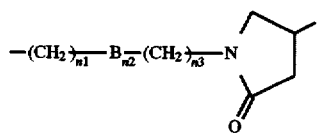

and mixtures thereof, wherein $R_6$ is as herein below defined, $n^1$ is zero or an integer from 1 to 12, $n^2$ is 0 or 1, $n^3$ is an integer from 1 to 5, and B is sulfur or oxygen with the proviso that when $n^2$ is 1, $n^1$ and $n^3$ each is at least 1; and with the further proviso that at least one of $R_5$ is a group of the formula:

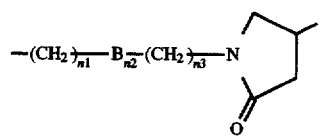

$R_6$ can be the same or different and can be selected from alkyl, aryl and olefin (vinyl);

$R_7$ and $R_8$, which can be the same or different, are selected from alkyl, aryl, capped or uncapped polyoxyalkylene, alkaryl, aralkylene and alkenyl (vinyl);

a can be an integer from 0 to 50,000;

b can be an integer from 0 to 5,000; and c can be an integer from 0 to 100;

$R_1$, which can be the same or different is of the group consisting of hydrogen and lower alkyl;

$R_2$ is hydrogen or an alkylene hydrocarbon group; and $R_3$ can be selected from -OH, -NH$_2$, $R_9$CONH-,$R_9$COO- and H, wherein $R_9$ is saturated or unsaturated alkyl having from 1–22 carbon atoms.

The novel imidazoline compositions of the present invention can be prepared by condensing under conditions of heating and stirring, either neat or in a solvent, a polysiloxane composition or fluid having at least one pyrrolidone-containing carboxyl functional group as is described in detail hereinafter (or a source thereof such as amides or esters of the acids) with an hydroxylalkyl ethylene diamine derivative, such as hydroxyethyl ethylene diamine. The mole ratio of the pyrrolidone-containing carboxyl functional polysiloxane composition to the diamine is variable but generally falls within the range of 1 mole of the carboxyl functional silicone composition to from 1 to about 2 moles, preferably about 1.1 to 1.6 moles of the diamine, followed by removal of excess diamine by distillation etc. The temperature at which the condensation reaction is carried out is generally in excess of 100° C., usually in the range of from about 120° C. to about 250° C. to 300° C., preferably greater than 140° C. The reaction time is several hours, usually within the range of about 4 to 12 hours, depending upon the particular reactants employed and the particular condensation temperature employed; or, where the reaction is carried out under less that atmospheric pressure, the reaction temperature may be somewhat reduced. Usually, the condensation temperature or temperature of heating and the duration of the heating are so correlated as to cause splitting out of water in excess of 1.5 moles, preferably 2 moles, for each mole of pyrrolidone-containing carboxyl group. In the case of complete reaction of the carboxyl groups, 2 moles of water will be evolved to form the product with an imidazoline nucleus.

The polysiloxane compositions or fluids having pyrrolidone-containing functional carboxyl groups or derivatives thereof (terminal, lateral or combination of terminal and lateral) applicable for use in preparing the silicone-containing imidazoline compositions of the invention can be readily prepared using known procedures such as disclosed in Ser. No.420,746 filed Apr. 12, 1995 by the reaction of corresponding silicone compositions or fluids having one or more functional primary amine groups with up to about one equivalent, preferably about stoichiometric quantities, of itaconic acid or its ester per functional primary amine group(s) at an elevated temperature for the time sufficient for substantially all of the itaconic acid or its ester to react with the functional primary amine group(s). In general from about 0.5, preferably from about 0.9 to about 1.1 equivalents of itaconic acid or its ester per functional primary amine group is reacted with the silicone fluid and polysiloxane compositions with at least one pyrrolidone-containing functional carboxyl group(s) and/or its ester are formed.

The reaction can be carried out neat or in an inert solvent such as alcohol, hydrocarbon solvent, chlorinated hydrocarbon and the like, as desired, in general, at elevated temperature, preferably from about 90° C. to about 130° C. The reaction readily proceeds and generally complete reaction of the itaconic acid or its ester with the available functional primary amine groups will occur in from about 1 to 5 hours.

Primary amine functional silicone fluids which are suitable for use have one or more primary amine functional groups(s) linked terminally, laterally or both terminally and laterally, as desired, are well known and are available commercially, for example, from Dow Corning, Th. Goldschmidt AG and Shin-Etsu. The equivalent weight of the silicone fluids or compositions which may be employed in the preparation of the carboxyl functional polysiloxane suitable for use in the present invention is not critical, and suitable compositions may have equivalent weights of 5,000 or even higher.

As indicated, the pyrrolidone-containing functional carboxyl polysiloxane compositions suitable for use in accordance with the present invention are readily prepared by reaction of primary amine functional silicone fluids with itaconic acid or its ester. Itaconic acid (methylene succinic acid) is a compound of the formula:

$$CH_2=C(COOR_9) CH_2 COOR_9$$

wherein, $R_9$ which can be the same or different, is hydrogen or lower alkyl (1-6 carbon atoms).

Suitable pyrrolidone containing carboxyl functional silicone compositions having terminal, lateral or combinations of terminal and lateral functional groups are available commercially, for example, from Mona Industries, Inc. While the molecular weight of the silicone compositions which may be employed is not critical, and suitable compositions may have carboxyl equivalent weights of 8000, or even higher, silicone compositions having carboxyl equivalent weights from about 1500 to about 15000 are in general preferred.

The hydroxyalkyl diamines or functional alkyl diamines, notably the lower functional hydroxy alkylene diamine, which are used to produce the imidazoline compositions of the invention, can likewise be selected from large numbers of known examples thereof, including aminoethylethanolamine or beta-hydroxyethyl ethylenediamine, aminoethyl ethylenediamine, N-methyl ethylene diamine, N-ethyl ethylene diamine and the like.

The novel acid salts of the silicone-containing imidazoline compositions of the invention can be represented by the following formula:

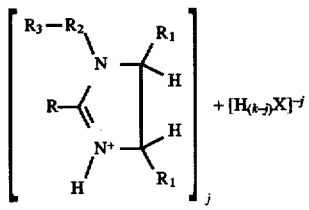

wherein:

R is an organosilicone backbone chain as hereinabove defined;

$R_1$ and $R_2$ are as hereinabove described;

$R_3$ is as hereinabove defined;

X is an anion group having 1-3 valence;

j is an integer from 1 to 3; and k is an integer from 1-3; with the proviso that (k-J) is 0 or a positive integer.

The acid salts of the aforementioned silicone-containing imidazoline compositions of the invention are readily prepared by simply admixing the imidazoline composition and an organic or mineral acid as illustrated below at temperatures between about room temperature and about 100° C., and preferably at ambient temperatures in the range of about 20° to 30° C. The imidazoline composition and acid reactants are desirably combined in approximately stoichiometric proportions, sufficient acid being added to substantially neutralize the amine groups present in the imidazoline composition as illustrated below:

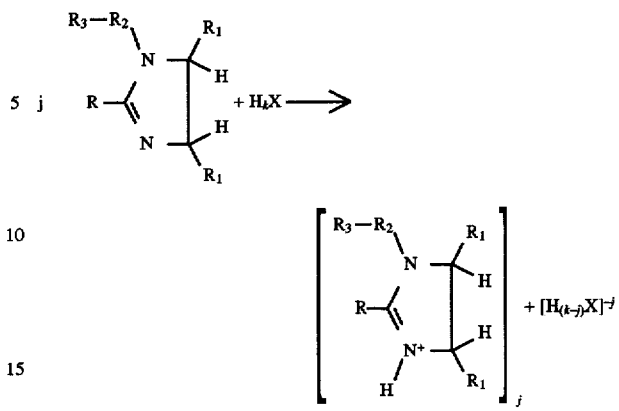

Illustrative of such suitable mineral and organic acids are phosphoric acid, phosphorous acid, sulfuric acid, sulfurous acid, hydrochloric acid, hypochlorous acid, acetic acid, carbonic acid, nitric acid, formic acid.

The imidazoline compositions of the present invention and acid salts thereof lend themselves to a wide variety of practical applications. Such materials can be employed for example, as emulsifier and dispersing agents, wetting agents and as additives to surface active compositions. They are also useful to provide improved substantivety to a variety of surfaces, as antistatic agents, foam stabilizers, as useful additives for metal cleaning and treating compositions and can be used to improve the lubricating and corrosion inhibition properties for metal treating compositions and in a variety of personal treating and cosmetic compositions.

Various other materials can be added to the novel silicone-containing imidazoline composition of the preset invention and the acid salts thereof. For example, such additives include various surface active agents; alkaline builder salts and agents such as sodium carbonate, sodium bicarbonate, sodium sulfate and the like, as well as special purpose additives such as dyes, bleaches, brighteners and the like.

The invention is further illustrated by the following examples which are not to be considered as limitative of its scope.

EXAMPLE 1

A Trimethylsilyl capped lateral (pendant) amino functional silicone fluid having an average molecule weight of about 3720 obtained from Shin-Etsu under the trade designation KE-864 is used in this example.

A mixture of 377 grams (0.1013 moles) of the silicone fluid and 13.2 grams (0.1013 moles) of itaconic acid is prepared in a reaction vessel and heated to a temperature of 160° for about two hours. A clear melt is formed having an acid number 11.6 (theoretical 14.6) which corresponds to a molecular weight of 4830.

241.8 grams (0.05 equivalent weight) of the silicone fluid prepared above and 15.6 grams of aminoethyl ethanolamine (0.5 mole a 50% excess) are charged to a reaction vessel with 50 ml of xylene and heated to reflux (about 170°) under nitrogen whereupon volatiles begin distilling off. The reaction mixture is heated for 6 hours over which time 4.5 ml of water is collected (theory -3.6 ml).

The reaction mixture is cooled to about 80° C. and a vacuum of 30 mm is applied to remove the solvent xylene. The temperature of the mixture is slowly raised to about 200° C. while reducing the pressure to a vacuum of about 3 mm as more volatiles are collected during which time unreacted aminoethyl ethanolamine distills over. The reaction mixture is then heated at 200° C. for two additional hours. After cooling an orange liquid is obtained having an alkali number of 13 (theory −11.4). An infra red scan confirms the presence of the imidazoline structure.

EXAMPLE 2

A Trimethylsilyl capped, pendant (lateral) amine functional silicone fluid having an average molecular weight of 4400 obtained from Shin-Etsu under the designation KF865 is used in this example.

88 grams (0.02 moles) of the silicone fluid is admixed with 2.6 grams of Itaconic acid (0.02 moles) and heated to a temperature of 130°–140° C. whereupon a clear melt is obtained and heating is continued for an additional two hours. The alkali number of the reaction product is less than 1 while the acid number is 13.2 (theoretical—12.4) which corresponds to a molecular weight of 4250.

127.5 grams (0.03 equivalents) of the silicone fluid from above is combined with 4.68 grams (0.045 moles–50% excess) of aminoethyl ethanolamine (AEEA) in a reaction vessel. The reaction mixture is heated to reflux (about 180° C.), removing water as it is formed. The temperature of the refluxing reaction mixture at which water is first evolved is about 145° C. and continues to about 165°–170° C. during which about 1.3 ml. of water is evolved in addition to some silicone volatiles. The reaction mixture is then cooled to about 100° C. and held under a vacuum while the temperature of the reaction mixture is raised. The vacuum is reduced to 3 mm while raising the temperature of the reaction vessel to about 190° C.

The reaction mixture is heated at 190° C. for 2 hours to remove excess AEEA. When cooled, an amber liquid is obtained having an alkali number of 16 (theory 13). An infra red scan of the reaction product is consistent with an imidazoline structure.

EXAMPLE 3

An alpha-omega Bis-aminoalkyl dimethyl polysiloxane fluid having an average molecular weight of about 1580 obtained from Shin-Etsu under the designation X-22162A is used in this example.

A combination of 994.5 grams (0.6296 moles) of the above silicone fluid and 163.7 grams (1.25 moles) of Itaconic acid is prepared in a reaction vessel and heated slowly to about 90° C. at which time an isotherm occurs which raises the reaction vessel temperature to 130° C. and water starts to evolve. The reaction mixture is heated to and maintained at a temperature of 140° C. to 150° C. for 3 hours during which time 20 ml of water and other volatiles are collected. A clear, yellow viscous liquid is formed having an alkali number of 0 and an acid number of 65.

The carboxyl functional silicone fluid from above is reacted with an excess of aminoethyl ethanolameni (AEEA) at a temperature of 180° C. while water is distilled from the reaction mixture.

The reaction mixture is cooled to about 80° C. and a vacuum of 30 mm is applied. The reaction mixture is slowly raised to 180°–190° C. while slowly reducing the pressure to a vacuum of about 3 mm during which time unreacted aminoethyl ethanolamine is removed and complete cyclization of the reaction product occurs. The reaction product is an orange liquid and an infra red scan confirms the structure of the reaction product as being consistent with imidazoline.

Although some preferred embodiments have been described, many modifications and variations may be made thereto in light of the above teachings. It is therefore to be understood that within the scope of the appended claims, the invention maybe practiced otherwise than as specifically described and illustrated.

What is claimed is:

1. Silicone containing imidazoline compositions represented by the formula:

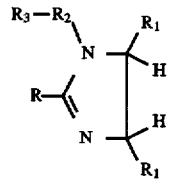

wherein:

R is a organosilicone chain represented by the formula:

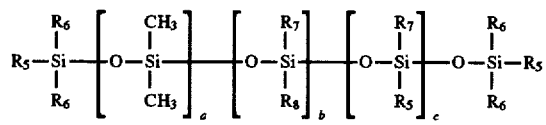

wherein:

$R_5$, which can be the same or different, is selected from $R_6$, a pyrrolidone-containing group of the formula:

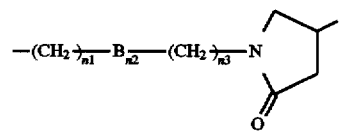

and mixtures thereof, wherein $R_6$ is as herein below defined, $n^1$ is zero or an integer from 1 to 12, $n^2$ is 0 or 1, $n^3$ is an integer from 1 to 5, and B is sulfur or oxygen with the proviso that when $n^2$ is 1, $n^1$ and $n^3$ each is at least 1; and with the further proviso that at least one of $R_5$ is a group of the formula;

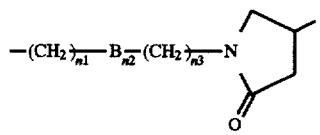

$R_6$ can be the same or different and is selected from alkyl, aryl or olefin;

$R_7$ and $R_8$, which can be the same or different are selected from alkyl, aryl, polyoxyalkylene, alkaryl, aralkylene and alkenyl;

a is an integer from 0 to 50,000;

b is an integer from 0 to 5,000;

c is an integer from 0 to 100;

$R_1$ which can be the same or different is of the group consisting of hydrogen and lower alkyl ($C_{1-6}$);

$R_2$ is hydrogen or an alkylene hydrocarbon group; and $R_3$ is selected from -OH, -NH$_2$, $R_9$CONH-, $R_9$COO- or -H, wherein $R_9$ is saturated or unsaturated alkyl having from 1–22 carbon atoms.

2. Acid salts of silicone-containing imidazoline represented by the following formula:

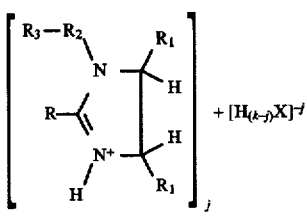

wherein:

R is a organosilicone chain represented by the formula:

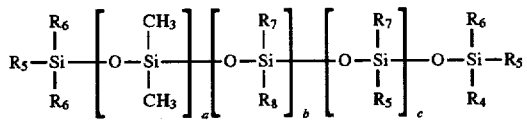

wherein:

$R_5$, which can be the same or different, is selected from $R_6$, a group of the formula:

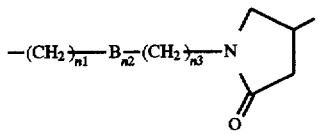

and mixtures thereof, wherein $R_6$ is as herein below defined, $n^1$ is zero or an integer from 1 to 12, $n^2$ is 0 or 1, $n^3$ is an integer from 1 to 5, and B is sulfur or oxygen with the proviso that when $n^2$ is 1, $n^1$ and $n^3$ each is at least 1; and with the further proviso that at least one of $R_5$ is group of the formula;

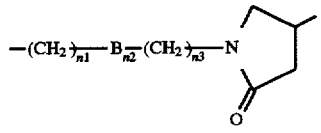

$R_6$ can be the same or different and is selected from alkyl, aryl and olefin;

$R_7$ and $R_8$, which can be the same or different, are selected from alkyl, aryl, polyoxyalkylene, alkaryl, aralkylene or alkenyl;

a is an integer from 0 to 50,000;

b is an integer from 0 to 5,000;

c is an integer from 0 to 100;

$R_1$ which can be the same or different is of the group consisting of hydrogen and lower alkyl;

$R_2$ is hydrogen or an alkylene hydrocarbon group;

$R_3$ is selected from -OH,-NH$_2$, -R$_9$CONH, R$_9$COO- and -H wherein $R_9$ is saturated or unsaturated alkyl having from 1–22 carbon atoms;

X is an anion group having 1–3 valence.

j is an integer from 1 to 3; and k is an integer from 1 to 3; with the proviso that (k-j) is 0 or a positive integer.

3. The silicone containing imidazoline compositions as claimed in claim 1, wherein the terminal $R_5$ groups are $R_6$ groups.

4. The acid salts of silicone-containing imidazoline compositions as claimed in claim 2, wherein the terminal $R_5$ groups are $R_6$ groups.

5. The silicone containing imidazoline compositions as claimed in claim 1, wherein the pendant $R_5$ groups are $R_6$ groups.

6. The silicone containing imidazoline compositions as claimed in claim 1, wherein the $R_6$, $R_7$ and $R_8$ are alkyl.

7. The silicon containing imidazoline compositions as claimed in claim 6, where the $R_6$, $R_7$ and R groups are methyl.

8. The silicone containing imidazoline compositions as claimed in claim 1, wherein $n^2$ is 0.

9. The acid salts of silicone-containing imidazoline compositions as claimed in claim 2, wherein $n^2$ is 0.

* * * * *